United States Patent [19]

Beard et al.

[11] Patent Number: 4,493,704
[45] Date of Patent: Jan. 15, 1985

[54] PORTABLE FLUID INFUSION APPARATUS

[75] Inventors: Robert W. Beard, Placerville; Russell F. Kirk, Sunnyvale, both of Calif.

[73] Assignee: OXIMETRIX, Inc., Mountain View, Calif.

[21] Appl. No.: 445,276

[22] Filed: Nov. 29, 1982

[51] Int. Cl.³ .............................................. A61M 5/20
[52] U.S. Cl. ..................................... 604/154; 604/224
[58] Field of Search ................ 604/155, 33, 121, 152, 604/154, 224; 121/DIG. 12

[56] References Cited

U.S. PATENT DOCUMENTS

| 4,300,554 | 11/1981 | Hessberg et al. | 604/135 |
| 4,313,439 | 2/1982 | Babb et al. | 604/135 X |
| 4,381,006 | 4/1983 | Genese | 604/135 |
| 4,430,079 | 2/1984 | Thill et al. | 604/154 |

Primary Examiner—Stephen C. Pellegrino
Attorney, Agent, or Firm—Robert S. Kelly

[57] ABSTRACT

A portable infusion device includes a disposable syringe which is located in a removable section of a compact package that comprises the device. In order to conserve space, a flexible piston rod assembly is provided wherein the syringe plunger head is connected to a thin flexible plunger stem which is reversely bent about the upstream end of the syringe body so that the outer end of the stem lies directly adjacent and parallel to the syringe body. A small motor located in the non-removable portion of the package drives the plunger through a screw which sequentially engages closely spaced teeth on the face of the plunger stem as it moves along the outer surface of the syringe. When the syringe contents have been discharged, the removable section, including the syringe and plunger stem assembly, can be readily removed and replaced.

24 Claims, 5 Drawing Figures

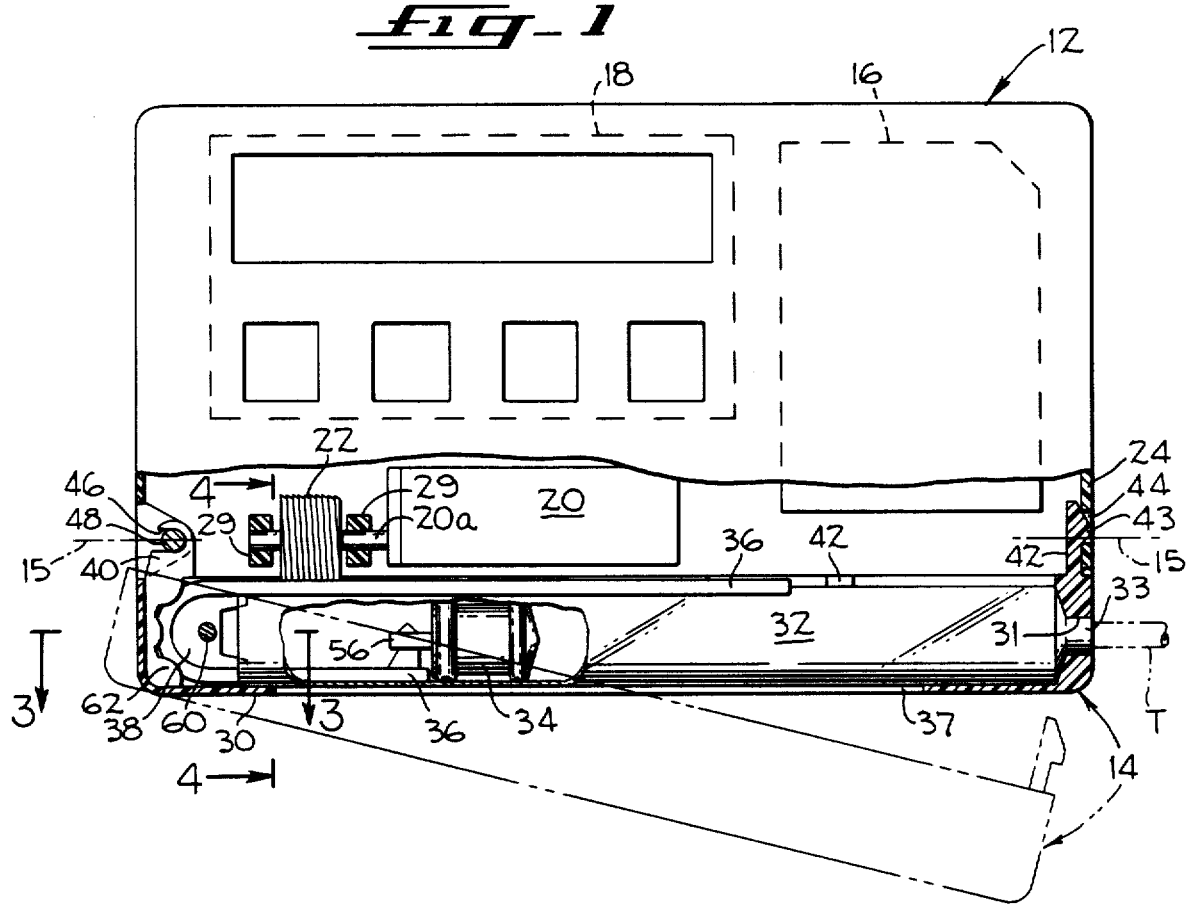
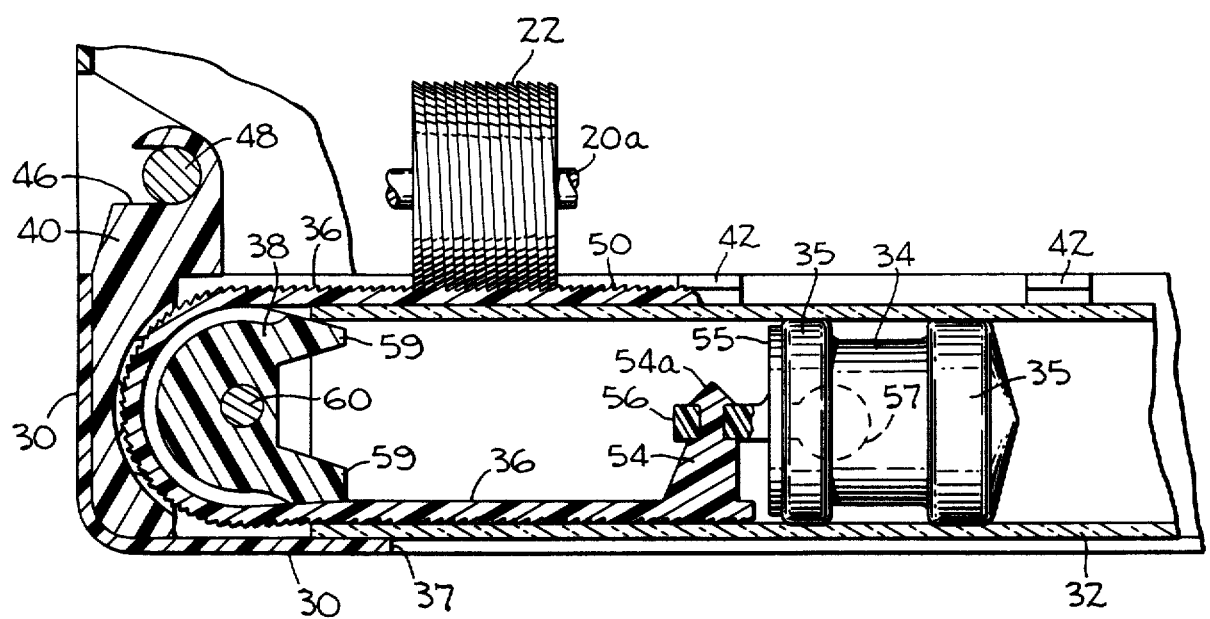

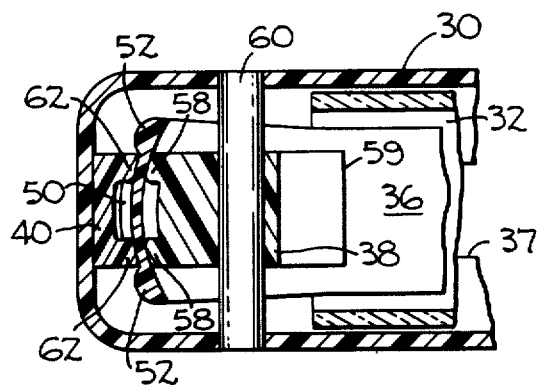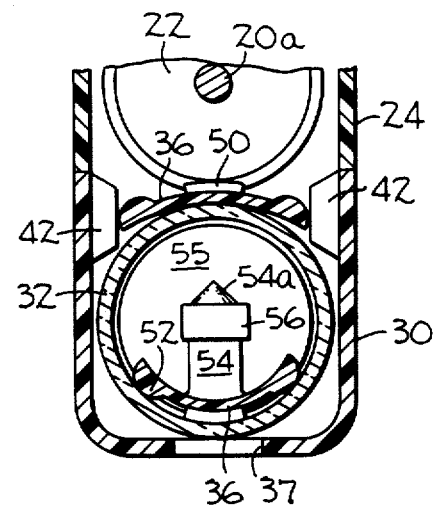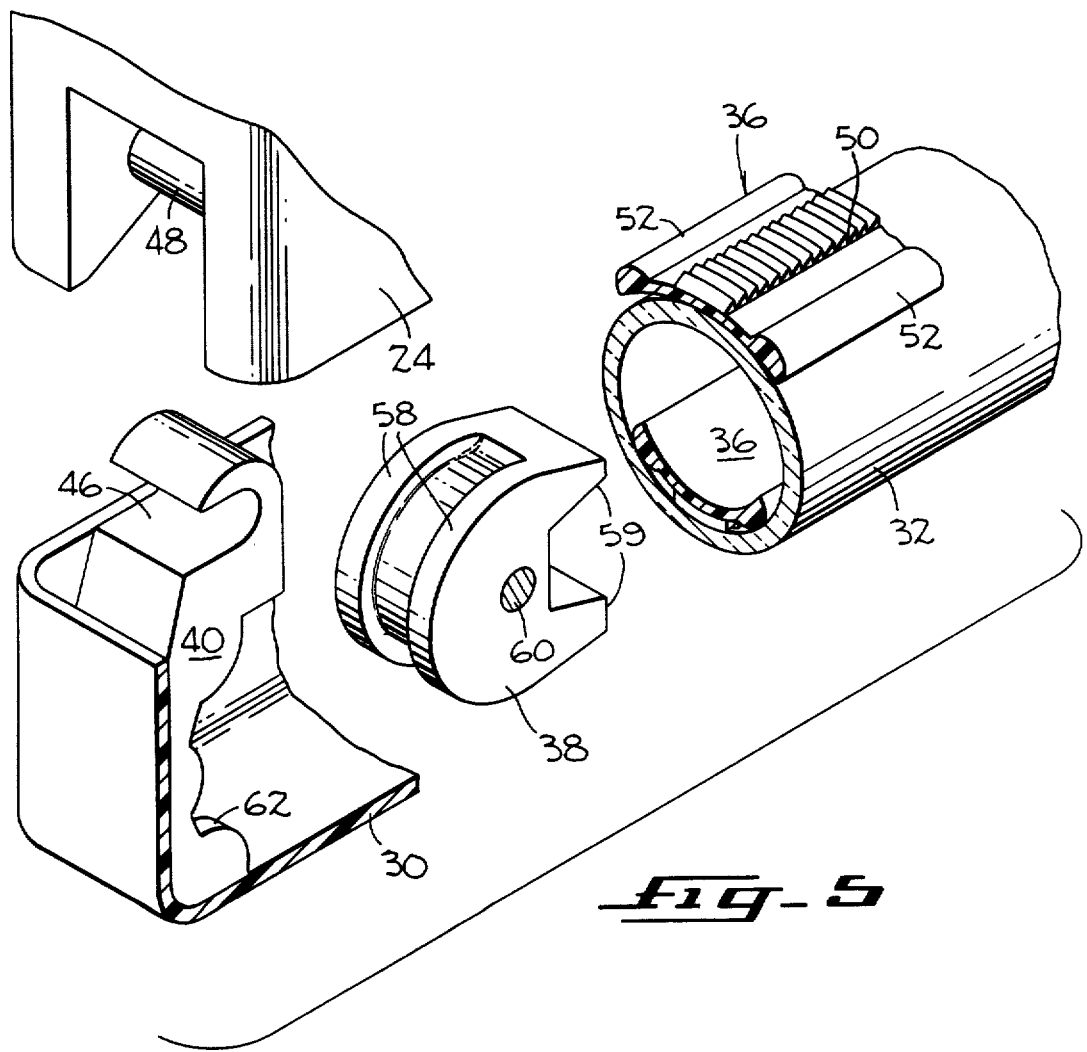

PORTABLE FLUID INFUSION APPARATUS

BACKGROUND OF THE INVENTION

1. Field of the Invention

The present invention pertains to fluid infusion apparatus for administering injectable liquid in a controlled manner to a patient, and more particularly, it pertains to fluid infusion devices of the portable type which are adapted to be used with ambulatory patients and outside of the normal hospital environment.

2. Description of the Prior Art

Infusion apparatus for injecting medications or life sustaining fluids intervenously into a patient have been in general use for many years in hospitals as is well known. Increasingly, such devices of a portable variety have been used where the patient is ambulatory. Thus, with a portable infusion device the patient may walk about the hospital grounds or the device may be used while the patient is at home or at work.

Generally speaking, portable infusion devices may be fairly small and compact so they can be carried by the patient without any obvious difficulties and so that he will not be seriously inconvenienced. Yet, such devices must be foolproof and capable of sustained accurate operation in any physical orientation and while the patient is rapidly moving about.

Portable infusion devices on the market today generally comprise two different types. One type uses a positive displacement pump or other conventional pump which automatically pumps small amounts of fluid from a reservoir into the patient on a predetermined schedule. The other type of device utilizes the more or less standard syringe and operates to drive the plunger of the syringe in a continuous or controlled intermittent manner, typically by the use of a lead screw or rack and pinion mechanism.

The U.S. patent to Szabo et al U.S. Pat. No. 3,886,938 discloses a portable fluid infusion device utilizing a standard syringe with a rack and pinion mechanism driving the plunger of such syringe through an appropriately controlled timing mechanism. Other rack and pinion drives for portable fluid injecting syringes can be found in the prior U.S. patents to Becker U.S. Pat. No. 4,231,368 and Smith U.S. Pat. No. 1,718,596—both of which disclose devices of the "hand gun" design.

A relatively compact portable infusion apparatus is disclosed in the U.S. patent to Hessberg et al U.S. Pat. No. 4,300,554 wherein a syringe is operated through a rack and pinion mechanism which is mounted in a closely spaced parallel arrangement with the syringe.

In yet another prior art portable infusion device, as disclosed in the U.S. patent to Babb et al U.S. Pat. No. 4,313,439, the plunger of a syringe is connected to a driving mechanism (either a compressed spring or a rack and pinion device) through a series of balls arranged in a U-shaped guide track so that the driving mechanism lies in parallel with the syringe and its plunger.

In all of the aforedescribed devices of the prior art, which utilize more or less standard fluid-injecting syringes, the apparatus must be made long enough in the dimension parallel to the body of the syringe so as to accomodate not only the syringe but also the full length of the plunger stem when the plunger is fully retracted in the syringe body.

SUMMARY OF THE INVENTION

With the portable fluid infusion apparatus of the present invention, a device is provided which can be packaged into a highly compact unit and yet which maintains the requisite characteristics of high accuracy and positive drive control in any physical orientation. This is accomplished by providing a flexible pusher member connected to the piston of a generally standard sized and shaped syringe which flexible member can be bent—preferably in a U-shaped path so as to lie closely adjacent and generally parallel to the body of the syringe. The flexible member is driven in a controlled manner for dispelling the liquid from the syringe. In view of the foregoing change in the manner in which the plunger head or piston is driven, the body of the syringe by itself, rather than the combined length of the syringe body and the plunger stem, determines the critical long dimension of the infusion apparatus package.

In another aspect of the present invention, it will be noted that the infusion apparatus package is comprised of a fixed portion and a disposable portion with the fixed portion comprising the basic drive and control devices and with the disposable portion including the syringe and the flexible drive arrangement therefor. When the two portions are connected the drive is automatically engaged with the flexible drive arrangement so that positive driving of the syringe piston is obtained. After each use by a patient the disposable portion of the package can be readily removed and replaced by a fresh unit.

BRIEF DESCRIPTION OF THE DRAWINGS

FIG. 1 is a top plan view of the portable infusion apparatus of the present invention with a portion thereof being broken away and shown in section and with the discharge position of the disposable portion of the apparatus being shown in phantom lines.

FIG. 2 is an enlarged longitudinal section through the drive portion of the portable infusion apparatus of FIG. 1.

FIG. 3 is an enlarged section taken along line 3—3 of FIG. 1.

FIG. 4 is an enlarged section taken along line 4—4 of FIG. 1.

FIG. 5 is an exploded view of the guide member and pivot connection at one end of the disposable portion of the infusion apparatus.

DESCRIPTION OF THE PREFERRED EMBODIMENT

The portable infusion apparatus of the present invention, as seen in FIG. 1, is comprised of a permanent portion 12 and a considerably smaller disposable portion 14 which is removably connected to the permanent portion along axis 15—15. The permanent portion of the apparatus generally includes a battery or power source 16, an electronic control means 18, a small DC motor 20 and a helical drive screw 22 which is attached to the drive shaft 20a of the motor. These items are each suitably mounted within a plastic casing 24 so as to comprise a thin rectangular package.

The electronic control means 18 of the present invention is entirely conventional and will not be described in detail herein. Briefly, the electronic control means includes a programable controller which can be operated to drive the DC motor 20 intermittently with variable on/off times and (typically) with relatively long off times relative to the on times so as to discharge a very small amount of fluid periodically to the patient over a long period of time.

The DC motor 20 is permanently mounted within the upper and lower walls of the casing 24 of the apparatus, and the drive shaft 20a thereof which supports the drive screw 27 is itself supported by a pair of guide blocks 29 which are also affixed to the flat upper and lower walls of the casing. It should be noted that the motor 20 includes suitable gearing to reduce the output drive to shaft 20a to a very low value so as to accommodate the normal low discharge dosages from the syringe.

The disposable portion 14 of the infusion apparatus will be seen to be comprised of casing 30 of the same thickness and length as that of the permanent portion casing 24 but of a considerably smaller width. Occupying the bulk of the space of the disposable portion is a syringe 32 having a conventional piston or plunger head 34 therein to propel the fluid therefrom. The syringe is of a conventional cylindrical shape and size having a 10 cc capacity with a 3.5-4 inch plunger stroke. A standard Luerlok fitting 33 is provided at the front end thereof for connection to the tubing T which extends to the injection needle (not shown). As seen in FIG. 1, the fitting 33 extends through an aperture 31 in the casing wall 30 so that the tubing T can be connected or disconnected as required.

Attached to the piston 34 is a flexible pusher tape 36 which will be seen to be reversely bent in a U-shape at the upstream or open end of the syringe so that the distal end of the tape lies adjacent to and in a position to ride upon the cylindrical body of the syringe 32 as the piston is moved (in the direction of the arrow in FIG. 1) within the body of the syringe. The outwardly extending face of the tape is engaged by the helical screw 27 so that rotation of the screw by the DC motor 20 propels the tape in its U-shaped path to drive the piston 34. In order to accomodate this flexible movement of the tape guides 38 and 40 are provided at the open end of the syringe to guide the tape in its critical 180° reverse turn, and a plurality of guides 42 (FIGS. 2 and 4) are provided along the body of the syringe to guide the trailing end of the tape as it is pushed along the outer surface of the syringe—the details of all of such guide members being described in greater detail hereinafter. A rectangular opening 37 is provided in the casing wall 30 adjacent to the syringe so that the fluid level therein can be monitored.

The disposable portion 14 of the infusion apparatus is removably attached to the permanent portion 12 by means of a simple connection which allows one end of the disposable portion to be readily snapped out of engagement with the permanent portion whereby the disposable portion can be rotated into the phantom line position shown in FIG. 1 and then easily separated for disposal or refilling. Thus, a flexible projecting member or tang 42 is provided to extend from one end of the casing wall 30 of the disposable portion, such tang having a laterally projecting nose 43 thereon which is adapted to be snapped into and retained by an aperture 44 in the casing wall 24 of the permanent portion of the apparatus when the tang is cammed past the edge of the casing wall 24 (FIG. 1) upon joining of the permanent and disposable portions. The opposite end of the disposable portion is provided with a rotatable connection which is obtained by a U-shaped groove provided at the upper projecting end of guide member 40 which groove is adapted to be received about a pin 48 that extends between the upper and lower flat surfaces of the casing 24 (see FIGS. 2 and 5). Thus, the separation axis 15 will be seen to lie along a line passing through the pivot pin 48 and the nose 43 that retain the disposable portion 14 at each end thereof.

It will be seen, therefore, that the disposable portion 14 can be separated from the apparatus by pushing (with one's finger or a pointed object) through the aperture 44 to bend the tang 42 inwardly and allow the front edge of the disposable portion to be swung out into the phantom line position in FIG. 1. In this latter position it is obvious that the guide member 40 can be readily separated from the supporting pivot pin 48 to completely disconnect the two sections. In assembling the apparatus, the reverse procedure is obviously used. Thus, the groove 46 of guide member 40 is assembled upon the pin 48, and the disposable portion casing is swung up into edge-to-edge engagement with the casing of the permanent portion with the tang 42 being bent back until the nose 43 snaps into place in the aperture 44.

It will be noted that the longest dimension of the infusion apparatus package is determined primarily by the length of the syringe 32. This syringe is generally of conventional shape and size as previously stated so as to contain the standard amount of medication or other fluid which may be normally used by the patient without requiring the reloading of the syringe. The thickness of the package will also be primarily determined by the thickness of the syringe body, as can be seen from FIG. 4, it being noted that one standard syringe generally has an internal diameter in the order of 0.45 inches. Finally, the width of the apparatus is primarily determined by the size of the electronic control circuity 18 and the battery 16 which perform the requisite control and drive of the syringe piston 34. It will be recognized that by limiting the longest dimension of the package, generally to the length of the syringe, a very compact and convenient device is provided which can be more easily carried by patients (in their pockets, for example) when they are ambulatory and which is generally easier to mount and store in any convenient place or position than are the devices of the prior art.

The flexible pusher tape 36, which comprises the basic feature of the present invention, is best shown in FIGS. 2-5. The tape is made of a readily flexible plastic material such as a molded polypropylene. In the preferred embodiment of the invention the tape will be approximately 0.040 inches thick (maximum dimension) and about 0.3 to 0.4 inches wide. A series of parallel grooves 50 are preformed in the face of the plastic tape along the narrow center portion thereof with the spacing being such that they can be engaged by the threads of the drive screw 22, as shown in FIG. 2, when the portions 12 and 14 of the apparatus are assembled. While the grooves may be formed at a slight angle transversely of the tape so as to match the pitch of the screw, since the pitch will be quite small (ideally, about 40 threads to the inch) it will be recognized that the threads may be formed transversely to the axis of the drive screw with the slight misalignment of screw threads and tape grooves being readily accommodated by the flexible nature of the plastic material of the tape. As seen in FIG. 5, the grooves 50 extend only for a short lateral distance at the center of the tape with enlarged beads 52 being provided at the lateral edges of the tape so as to both lend strength to the tape and maintain it in its U-shaped path as it traverses the open end of the syringe about the fixed guide member 38.

The leading end of the pusher tape 36 is provided with an integral upright projection 54 which includes a conical nib 54a at the upper end thereof (FIG. 2) that is adapted to be snapped into an aperture in a connector plug 56 attached to the piston 34. Thus, the connector plug has an enlarged end 57 which is received within the body of the piston to secure it. Also attached to the connector plug 56 is a rigid plate 55 which is received upon the trailing face of the piston and serves to rigidify the connection between the connector plug and the piston. As can be seen from FIGS. 4 and 5, the pusher tape 36 will enter the open end of the syringe body as the piston expels the fluid therefrom, and the tape will be further flexed into a tighter arcuate shape by the internal cylindrical wall of the syringe. The piston 34 is conventional and is formed of soft rubber or rubberlike material with enlarged radially extending portions 34a which are adapted to seal against the inner surface of the syringe body so as to prevent the flow of fluid therepast.

The guides 38, 40 and 42 (FIG. 2) operate to continuously and precisely maintain the pusher tape 36 in its path so that the drive from the screw 22 will be in precise increments. This, of course, is necessary since it is of considerable importance in infusion apparatus that the dosages injected into the patient be accurate. Thus, the inner guide 38 will be seen to include a pair of radially projecting flanges 58 which are adapted to engage the inner arcuate face of the pusher tape to support it throughout its 180 degree reverse movement (FIG. 3). Guide 38 further includes projecting portions 59 which fit within the open end of the syringe body 32 to secure the syringe tightly in place within the casing 30 of the disposable portion 14 of the apparatus. Guide 38 is attached within the casing 30 by means of a pin 60 that is affixed to the guide member and to the flat upper and lower walls of the casing.

The outer guide 40, which is secured to the transverse end face of the disposable portion casing 30 (FIG. 5), will be seen to be generally U-shaped (FIG. 3) in cross-section and to include a pair of projecting flanges 62 which are adapted to be received within the recesses formed in the pusher tape 36 between the outer beads 52 and the grooved center portion 50 thereof so as to force the pusher tape against the flanges 58 of the inner guide 38 (FIG. 3). The spacing between flanges 62 and 58 is just enough to allow the plastic pusher tape to slide freely therebetween but not to permit any substantial lateral movement of the tape so as to introduce errors into the linear positioning of the tape. The outer guide flanges 62 are lobed (FIGS. 2 and 5).

Guides 42, which are affixed along the inner faces of the casing 30, are arranged at uniform intervals so as to prevent any lateral shifting of the tape as it is moved along the face of the syringe. These guides, best seen in FIG. 4, thereby loosely guide the outer beads 52 of the pusher tape and maintain the lateral alignment of the tape particularly in that critical area just upstream of the drive screw 22.

Operation of the infusion apparatus of the present invention will be seen to be fairly simple. With the disposable portion 14 removed from the remainder of the apparatus, the flexible pusher tape 36 can be pulled back so as to retract the plunger head 34 within the syringe 32 while the tubing T containing the injection needle (not shown) is inserted into the liquid to be injected. This results in the liquid being pulled into the syringe through the Luerlok fitting 33.

The operation is obviously continued until the piston 34 is fully retracted so as to fill the syringe with liquid. Then, the tape 36 is pushed down between the guides 42, and the U-shaped groove 46 is mounted upon the pin 48 of the permanent portion 12 of the apparatus. Finally, the casing 30 is swung from the outwardly pivoted position (FIG. 1) until the nose 43 of tang 42 snaps within the aperture 44 in the casing 24 to securely lock the portions in place. The control circuitry 18 can then be operated to drive the screw 27 in the programmed manner so as to cause the piston 34 to incrementally push the liquid from the syringe.

It will be seen that the portable infusion apparatus of the present invention is relatively simple in nature and yet includes a positive drive arrangement which provides accurate and thoroughly reliable operation. Most importantly, by eliminating the conventional piston rod or plunger stem for the plunger of the syringe, the necessary space required for the apparatus is considerably reduced; hence, the apparatus may be contained in a very compact and efficient package which can readily be carried within a patient's pocket, for example, so as to render it highly convenient to use.

Although the best mode contemplated for carrying out the present invention has been herein shown and described, it will be apparent that modification and variation may be made without departing from what is regarded to be the subject matter of the invention.

What is claimed is:

1. Portable fluid infusion apparatus comprising a syringe for holding a predetermined quantity of an injectable liquid to be delivered to a patient, a piston within the body of the syringe for ejecting liquid therefrom, a flexible member connected to said piston within the body of the syringe and extending in a path bent sharply away from the axis of the syringe, and means for driving the flexible member into the body of the syringe in a controlled manner for dispelling said liquid from the syringe.

2. Portable fluid infusion apparatus as set forth in claim 1 wherein said flexible member is reversely bent so as to lie adjacent to and generally parallel to the body of the syringe.

3. Portable fluid infusion apparatus as set forth in claim 1 wherein said flexible member comprises a generally flat member having a series of indentations thereon, said means for driving including a member having projections thereon for serially engaging the indentations on said flexible member to urge it along said path.

4. Portable fluid infusion apparatus as set forth in claim 3 wherein said indentations in said flexible member comprise grooves and wherein said means for driving includes a screw mounted for engagement with said grooves.

5. Portable fluid infusion apparatus as set forth in claim 2 wherein said flexible member has a generally flat shape with a series of short parallel grooves in the flat face thereof and wherein said drive means comprises a screw mounted upon a shaft extending parallel to said flexible member and said syringe.

6. Portable fluid infusion apparatus as set forth in claim 2 wherein said flexible member comprises a generally flat member, and guide means confining said flexible member to ride along the face of said syringe in said path.

7. Portable fluid infusion apparatus as set forth in claim 6 wherein said flexible member has a series of indentations therein and wherein said means for driving includes a member having projections thereon for serially engaging the indentations on said flexible member to urge it along said path.

8. Portable fluid infusion apparatus as set forth in claim 6 wherein said strip is arcuate in transverse cross section so as to generally conform to the curvature of the body of the syringe.

9. A portable fluid infusion device comprising a package including a permanent portion and a disposable portion, said permanent portion including a power supply, a motor, and control means for operating the motor, said disposable portion comprising a syringe including a piston operable within the body of the syringe for expelling fluid therefrom, and flexible pusher means positioned closely adjacent to and parallel with the body of the syringe for moving the piston within said syringe body, said syringe extending for substantially the full length and width of the disposable portion whereby said means for moving the piston comprises a relatively small volume of the disposable portion, said disposable portion further including means for removably connecting the disposable portion to the permanent portion so that said means for moving the piston operatively engages said motor when said portions are connected.

10. A portable fluid infusion device as set forth in claim 9 wherein said flexible pusher means comprises a resilient pusher element connected at its inner end to said piston and bent in a U-shaped path so as to lie closely adjacent to the body of the syringe at its outer end.

11. A portable fluid infusion device as set forth in claim 10 wherein said pusher element has spaced indentations thereon adapted to be engaged by said motor.

12. A portable fluid infusion device as set forth in claim 9 wherein said means for connecting includes a rotatable connection allowing the disposable portion to be swung away from the permanent portion before being detached therefrom.

13. For use with a portable infusion apparatus that includes a drive means and means for controlling the drive means to control the amount of an injectable liquid delivered to a patient, a disposable syringe for holding a predetermined quantity of said liquid, a piston within the body of the syringe for ejecting liquid thereform, and a flexible member connected to said piston, and guide means for constraining said flexible member to extend in a path bent sharply away from the axis of the syringe, said flexible member having means thereon adapted for engagement by said drive means to propel said piston.

14. Apparatus as set forth in claim 13 wherein said guide means constrains said flexible member to extend in a reversely bent path so as to lie adjacent to and generally parallel to the body of the syringe.

15. Apparatus as set forth in claim 14 wherein said flexible member comprises a generally flat resilient member having a series of indentations thereon comprising said means adapted for engagement by said drive means.

16. Apparatus as set forth in claim 15 wherein said indentations comprise short parallel grooves adapted to be engaged by the threads of a screw.

17. Apparatus as set forth in claim 14 wherein said strip is arcuate in transverse cross section so as to generally conform to the curvature of the body of the syringe.

18. Apparatus as set forth in claim 13 including a casing surrounding said syringe and flexible member, and means for removably fastening said casing to the drive means.

19. Apparatus as set forth in claim 18 wherein said fastening means includes a rotatable connection permitting said casing to be swung away from the drive means before being detached therefrom.

20. For use with a portable infusion apparatus that includes a drive means and means for controlling the drive means to control the amount of an injectable liquid delivered to a patient, a disposable syringe for holding a predetermined quantity of said liquid, a piston within the body of the syringe for ejecting liquid therefrom, a flexible pusher member rigidly connected to said piston, said pusher member having a flexibility such that it can be flexed into a path sharply diverging from the axis of the syringe, and means on said pusher member for adapting the member for engagement over the major portion of its length with said drive means in order to propel said piston within the body of the syringe.

21. Apparatus as set forth in claim 20 wherein said pusher member comprises a generally flat resilient member having a series of indentations thereoon.

22. Apparatus as set forth in claim 21 wherein said indentations comprise short parallel grooves adapted to be engaged by the threads of a screw.

23. Apparatus as set forth in claim 20 including guide means mounted at the open end of said syringe for forcing said pusher member into a 180 degree turn and for confining the free end of said pusher member to ride along the face of said syringe.

24. Apparatus as set forth in claim 23 wherein said pusher member is arcuate in transverse cross section so as to generally conform to the curvature of the body of the syringe.

* * * * *